United States Patent [19]

Diamond

[11] 4,120,947
[45] Oct. 17, 1978

[54] XANTHINE COMPOUNDS AND METHOD OF TREATING BRONCHOSPASTIC AND ALLERGIC DISEASES

[75] Inventor: Julius Diamond, Morris Plains, N.J.

[73] Assignee: Cooper Laboratories, Inc., Parsippany, N.J.

[21] Appl. No.: 672,388

[22] Filed: Mar. 31, 1976

[51] Int. Cl.² .................... C07D 473/06; A61K 31/52
[52] U.S. Cl. ...................................... 424/45; 424/253; 544/271; 544/273; 544/311; 544/312
[58] Field of Search ............... 260/256, 254; 424/253, 424/45

[56] References Cited

U.S. PATENT DOCUMENTS

| 2,729,643 | 1/1956 | Stoll et al. ............................ 260/256 |
| 3,632,742 | 1/1972 | Eckert et al. ......................... 260/256 |

OTHER PUBLICATIONS

Cutting, handbook of Pharmacology, 4th Edition, pp. 294–296.
Giari et al. - II Farmaco-Ed. Sc. 12(12): 1016–1024, (1957).
Vieth et al. - Biochem. Zeitschr. 163, 13–26, (1925).

*Primary Examiner*—Leonard Schenkman
*Attorney, Agent, or Firm*—John J. Kolano; Thomas R. Boland

[57] ABSTRACT

Bronchial asthma and other bronchospastic and allergic diseases are treated by administering an effective amount of a substituted xanthine compound having the formula:

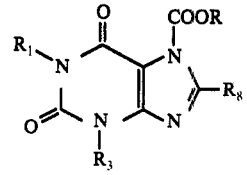

wherein:
$R_1 = C_1–C_3$ alkyl,
$R_3 = C_1–C_7$ alkyl, $C_3–C_7$ alkenyl, $C_3–C_7$ alkynyl, $C_3–C_7$ cycloalkyl or $C_4–C_7$ cycloalkylalkyl,
$R_8 = H$, $C_1–C_4$ alkyl, $C_3–C_4$ alkenyl, $C_3–C_4$ alkynyl or $C_3–C_4$ cycloalkyl,
$R = C_1–C_4$ alkyl, 2-halo $C_2–C_3$ alkyl, or phenyl Novel and preferred bronchodilator and antiallergy compounds are disclosed having the formula

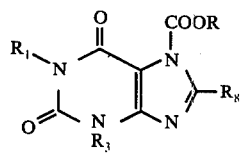

wherein:
$R_1 = C_1–C_2$ alkyl
$R_3 = CH_2–(C_3–C_4$ alkyl$), —CH_2—(C_3–C_4$ alkenyl), or $—CH_2—(C_3–C_4$ cycloalkyl)
$R_8 = H$, $C_1–C_2$ alkyl,
$R = C_1–C_4$ alkyl, 2-halo $C_2–C_3$ alkyl, or phenyl The bronchodilator and antiallergy agents may be administered in the form of tablets, capsules or aerosols.

48 Claims, No Drawings

XANTHINE COMPOUNDS AND METHOD OF TREATING BRONCHOSPASTIC AND ALLERGIC DISEASES

BACKGROUND OF THE INVENTION

This invention relates to methods for treatment of bronchial asthma and other bronchospastic and allergic diseases. More particularly it relates to a method of treating these diseases employing certain substituted xanthine compounds.

Bronchial asthma is characterized by bronchospasm caused by contraction of the bronchial smooth muscle, increased secretion of mucus from the bronchi, and edema of the respiratory mucosa. While the etiology of asthma is not completely known, it is believed to involve an allergic reaction. Allergic reactions occur in sensitized individuals who are exposed to the antigen to which they are sensitized. The antigen provokes the release in the body of certain chemicals (allergic mediators) which in turn produce the allergic symptoms. Allergic reactions can also produce effects in organs other than the bronchi, particularly the skin, eyes and nasal mucosa and include such diseases as allergic rhinitis and urticaria.

Acute asthmatic bronchospasm has been treated with drugs which relax bronchial smooth muscle. Sympathominmetic drugs such as epinephrine, isoproterenol, and terbutaline and xanthine drugs such as theophylline and its salts (aminophylline, etc.) have been used for this purpose. Drugs such as cromolyn sodium which inhibit the release of allergic mediators, have been used prophylactically to treat bronchial asthma. Corticosteriod drugs have also been used to treat bronchial asthma and other allergy diseases.

Many of the drugs used hitherto have shortcomings which make them less than ideal for treatment of asthma and other bronchospastic and allergic diseases. For example, epinephrine and isoproterenol relieve the symptoms of asthma for only a relatively short period of time and are ineffective orally. Theophylline has limited efficacy and produces cardiac and gastrointestinal side effects. Cromolyn sodium is only effective by inhalation or injection and is ineffective by oral administration. The corticosteriod drugs have serious side effects which limit their chronic use.

Substituted xanthines have been known for some time as bronchodilators, and theophylline (1,3-dimethylxanthine) has long been used in the treatment of bronchial asthma.

Prior attempts have been made to improve theophylline by substituting the xanthine nucleus with different groups in several positions in the molecule. A number of 1,3-dialkylxanthines and 1,3,8-trialkylxanthines have been shown to be bronchodilators in animal models. However, none of the substituted xanthine compounds hitherto synthesized have displaced theophylline and its salts as clinically useful bronchodilator and antiallergy agents. There are several references in the prior art disclosing the synthesis of compounds which may be considered structurally similar to the compounds of the claimed invention. However, in each case where such similarity exists, either the degree and/or duration of activity of the claimed compounds is far superior to those of the prior art or a completely different utility is disclosed in connection with the prior art compounds. Stoll (Stoll, J. H., et.al., U.S. Pat. No. 2,729,643, issued Jan. 3, 1956), for example, discloses a method for forming substituted xanthines which are said to be effective as diuretics. At one stage in the Stoll process, an intermediate compound is formed which is illustrated by Stoll in the form of a generic structural formula, although the only specific example of a compound within the context of the general formula is 1,3-diethyl-7-carboethoxyxanthine. There is no specific disclosure of a 1,3,8-trialkyl-7-carboalkoxyxanthine, nor is there any disclosure in the patent of a 3-(2-methyl-1-butyl) substituted xanthine. Certain compounds disclosed by Vieth (Vieth, H., et.al., Biochem. Z. 163, 13–26 (1925).), Cacace, (Cacace, F., et.al., Ann. Chim. (Rome) 45, 983–993 (1955).), Giani, (Giani, M., et.al., Farmaco (Pavia), Ed. Sci. 12, 1016–1024 (1957).), may also be construed as being structurally similar to the compounds of this invention, but again none of these references suggests a bronchodilating or antiallergen use. They all acknowledge the diuretic use of theophylline derivatives although Cacace and Giani have no disclosure of a utility for the 7-carboalkoxy compounds discussed therein. Armitage, (Armitage, A. K., et.al., Brit. J. Pharmacol., 17, 196–207 (1961).), and Goodsell, (Goodsell, E. G. et.al., J. Med. Chem. 1971, 14 (12) 1202–1205.), both of whom deal with di- and tri-alkyl xanthines, allege uses relating to bronchodilation, but neither reference shows a 7-carboalkoxy substituent on a xanthine nucleus and substitution in the 3-position does not include a 2-methyl-1-butyl grouping. Thus, while a similar use is involved, the compounds of this invention are not suggested by these prior art compounds. This is especially so in light of Beavo's disclosure (Beavo, J.A., et.al., Mol. Pharmacol. 1970, 6 (6) 597–603) that in studying the adenosine 3', 5' monophosphate phosphodiesterase (PDE) inhibiting activity of substituted xanthines, which is generally conceded to be correlated with bronchodilation activity, he noted that substitution in the 7-position either has no affect or decreases the potency of the compounds tested.

A class of substituted xanthine compounds has now been found which are very effective bronchodilator and antiallergy agents with rapid onset and prolonged duration of action. These compounds are effective, rapid-acting bronchodilators by all routes of administration and accordingly can be used to abort an acute bronchospastic attack. In addition, they are orally effective, long-acting antiallergy compounds, by suppressing the release of allergic mediators. Hence, these compounds may be used prophylactically to treat bronchial asthma, and other bronchospastic and allergic diseases.

SUMMARY OF THE INVENTION

It is an object of this invention to provide a method of treating bronchial asthma and other bronchospastic and allergic diseases. A further object is to provide a method for treating bronchial asthma and other bronchospatic and allergic conditions by administering drugs comprising substituted xanthines. A further object is to provide a method of treatment which may be used prophylactically as well as in acute bronchospastic and allergic attacks. A further object is to provide a method for producing long-lasting relief of bronchial asthma and other bronchospastic and allergic diseases. A further object is to provide novel compounds for the treatment of bronchial asthma and other bronchospastic and allergic diseases. According to this invention bronchial asthma and other bronchospastic and allergic diseases are treated by administering an effective amount of a substituted xanthine compound having the formula:

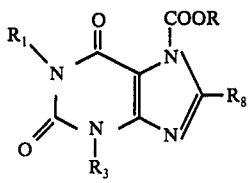

wherein:
$R_1 = C_1-C_3$ alkyl,
$R_3 = C_1-C_7$ alkyl, $C_3-C_7$ alkenyl, $C_3-C_7$ alkynyl, $C_3-C_7$ cycloalkyl or $C_4-C_7$ cycloalkylalkyl,
$R_8 = H$, $C_1-C_4$ alkyl, or $C_3-C_4$ cycloalkyl,
$R = C_1-C_4$ alkyl, 2-halo $C_2-C_3$ alkyl or phenyl These compounds may be administered orally, parenterally, or by inhalation in the form of tablets, capsules, solutions, elixirs, emulsions, aerosols and the like. Typical effective doses in man range from 0.01 to 50 milligrams per kilogram of body weight depending on route of administration and potency of compound selected. The novel compounds of this invention which are preferred as bronchodilator and antiallergy agents have the following formula:

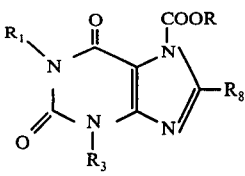

wherein:
$R_1 = C_1-C_2$ alkyl,
$R_3 = CH_2(C_3-C_4$ alkyl$)$, $-CH_2-(C_3-C_4$ alkenyl$)$, or $-CH_2-(C_3-C_4$ cycloalkyl$)$,
$R_8 = C_1-C_2$ alkyl
$R = C_1-C_4$ alkyl, 2-halo $(C_2-C_3$ alkyl$)$, phenyl

DESCRIPTION OF PREFERRED EMBODIMENTS:

Suitable groups for $R_1$ in the compounds used in the method of treatment of this invention include methyl, ethyl, n-propyl and isopropyl. Suitable groups for $R_3$ include methyl, ethyl, n-propyl, i-propyl, n-butyl, i-butyl, 1-methyl-1-propyl, n-pentyl, 1-methyl-1-butyl, 2-methyl-1-butyl, 3-methyl-1-butyl, 2,2-dimethyl-1-propyl, n-hexyl, 1-methyl-1-pentyl, 2-methyl-1-pentyl, 3-methyl-1-pentyl, 4-methyl-1-pentyl, 2,2-dimethyl-1-butyl, 2,3-dimethyl-1-butyl, 3,3-dimethyl-1-butyl, 1-ethyl-1-butyl, 2-ethyl-1-butyl, n-heptyl, 1-methyl-1-hexyl, 2-methyl-1-hexyl, 3-methyl-1-hexyl, 4-methyl-1-hexyl, 5-methyl-1-hexyl, 1,2-dimethyl-1-pentyl, 2,2-dimethyl-1-pentyl, 2,3-dimethyl-1-pentyl, 1,3-dimethyl-1-pentyl, 2,4-dimethyl-1-pentyl, 1-ethyl-1-pentyl, 2-ethyl-1-pentyl, 2-ethyl-3-methyl-1-pentyl, cyclopropyl, cyclobutyl, cyclopentyl, cyclohexyl, allyl, methallyl, 2-methyl-2-buten-1-yl, 2-methyl-3-buten-1-yl, 3-methyl-2-buten-1-yl, propargyl, 2-methyl-3-butyn-1-yl, cyclopropylmethyl, cyclobutylmethyl, cyclopentylmethyl, cyclohexylmethyl and 2-cyclopropylethyl and the like.

Suitable groups for $R_8$ include methyl, ethyl, n-propyl, isopropyl, n-butyl, isobutyl, 1-methylpropyl, t-butyl, cyclopropyl and cyclobutyl.

Suitable groups for R include methyl, ethyl, n-propyl, isopropyl, n-butyl, isobutyl, 2-chloroethyl, 2-chloropropyl, 3-chloropropyl, 2-bromoethyl, 2-bromopropyl, 3-bromopropyl and phenyl. In this application the term "halo" signifies either chlorine or bromine.

With respect to the xanthine compounds of the prior art, the introduction of the carboalkoxy group in the 7-position of the compounds of this invention has been found to give an improvement in efficacy. For example, as shown below in Example 5, 1,3-dimethyl-7-carbomethoxyxanthine, i.e., 7-carbomethoxytheophylline or theophylline-7-carboxylic acid, methyl ester, is significantly more effective than theophylline itself. The data show that the xanthine carboxylate ester is more potent, with both faster onset and longer duration of action. These data indicate a greater bioavailability of the xanthine carboxylate ester. The 7-carboalkoxyxanthines are believed to act as latent forms of the alkylxanthine bronchodilators and are biotransformed to the corresponding xanthine-7-carboxylic acids, which then decarboxylate to yield the corresponding alkylxanthine. Thus for the case of 1,8-dimethyl-3-(2-methylbutyl)-xanthine-7-carboxylic acid, methyl ester, the major reaction sequence is thought to proceed as follows:

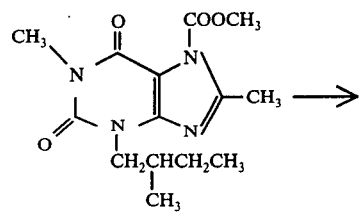

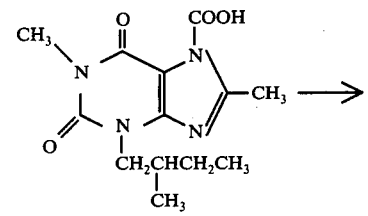

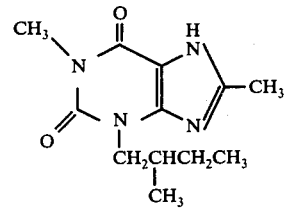

It is preferred to have $R_8$ = methyl. The introduction of an alkyl group in the 8-position of the xanthine nucleus has been discovered to produce a compound having a long lasting activity. As shown below in Example 6, all of the 8-alkylxanthine bronchodilators have a longer duration of activity than the corresponding 8-H xanthine. It is believed that the 8-alkyl groups prevents the normal enzymic oxidation at the 8-position of xanthines and thereby prevents rapid bioinactivation of the xanthine.

It is preferred to have $R_3$ selected from the group consisting of methyl, ethyl, n-propyl, n-butyl, isobutyl, n-pentyl, 2-methyl-1-butyl, 3-methyl-1-butyl, 2,2-dimethyl-1-propyl, n-hexyl, 2-methyl-1-pentyl, 3-methyl-1-pentyl, 4-methyl-1-pentyl, 2-methyl-1-hexyl, methallyl, cyclopropylmethyl, cyclobutylmethyl, and 2-cyclopropylethyl groups. More preferred $R_3$ groups are isobutyl, 2-methyl-1-butyl, 2-methyl-1-pentyl, 3-methyl- 1-butyl, n-pentyl, 2,2-dimethyl-1-propyl, methallyl, cyclopropylmethyl and cyclobutylmethyl groups. Of these the isobutyl and 2-methyl-1-butyl are most preferred and 2-methyl-1-butyl is uniquely preferred. This group has never been reported as a substituent in a xanthine compound and has a significant advantage over the prior art $R_3$ groups. In Comparison with the known $R_3$ groups, as shown below in Example 7, the 2-methyl-1-butyl group surprisingly confers on the xanthine bronchodilators an effectiveness equal to the best $R_3$ group reported in the prior art, the isobutyl group. This is surprising because the next higher homolog, the 2-methyl-1-pentyl group, confers much lower bronchodilation potency. Furthermore, the 2-methyl-1-butyl group surprisingly combines this great potency with a substantially lower toxicity. Thus the 2-methyl-1-butyl group is uniquely suitable for the $R_3$ group of a xanthine bronchodilator, particularly in combination with a 7-carboalkoxy group which, as previously indicated, increases the efficacy of the compound, and therefore such compounds which contain the 2-methyl-1-butyl group are greatly preferred.

Thus the preferred groups for $R_1$, $R_8$ and R are methyl. The most preferred group for $R_3$ is 2-methyl-1-butyl. The most preferred compound is that which combines all four preferred groups, namely 1,8-dimethyl-3-(2-methyl-1-butyl)-7-carbomethoxyxanthine.

The 1,3,8-trialkyl-7-carboalkoxyxanthines of this invention may be prepared by reacting the sodium salt of the corresponding 1,3,8-trialkylxanthine with an alkyl chloroformate ClCOOR According to the following reaction:

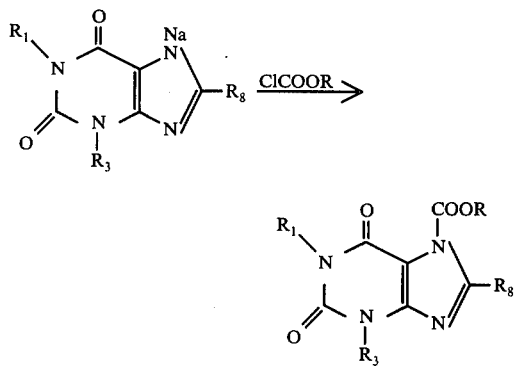

The sodium salt of the 1,3,9-trialkylxanthine can be prepared by the action of a strong base such as sodium hydride on the 1,3,8-trialkylxanthine. The reaction can be carried out in a suitable inert solvent such as tetrahydrofuran.

The 1,3,8-trialkylxanthines can be prepared by the well-known general procedure of Traube, Berichte 33, 1371 and 3055 (1900).

A 1,3-dialkyl urea having the general formula

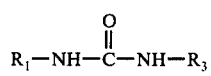

is first prepared. This urea can be prepared by reacting one mole of an alkyl isocyanate with one mole of an amine according to the reaction

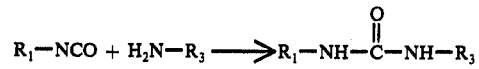

It is evident from the symmetry of the product that either $R_1$ or $R_3$ may be in the isocyanate reagent and either group may be in the amine reagent. The conditions under which this well-known reaction proceeds are known to one skilled in the art.

The isocyanate required for the above reaction may be prepared by reacting the corresponding amine with phosgene according to the equation

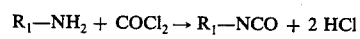

The conditions for this reaction are well known to those skilled in the art and are described in the chemical literature, e.g., in British Pat. No. 901,337.

The 1,3-dialkyl urea is next converted into a 1,3-dialkyl-1-cyanoacetylurea by reaction with cyanoacetic acid according to the following reaction:

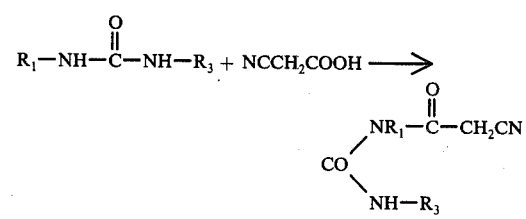

The reaction is conveniently carried out in acetic anhydride at 60° to 70°. The reaction gives preferentially although not exclusively the product containing the smaller alkyl group as $R_1$. The isomers may be separated by fractional crystallization. The 1,3-dialkyl-1-cyanoacetylurea is next cyclized to form a 4-amino-1,3-dialkyluracil according to the following reaction:

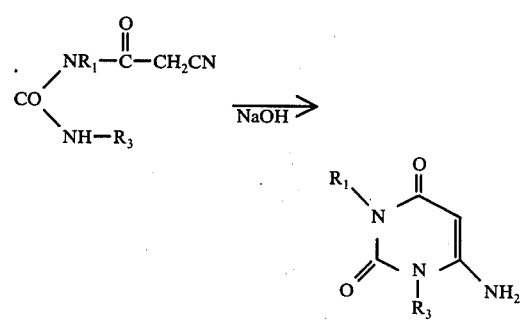

The reaction is carried out by treating the 1,3-dialkyl-1-cyanoacetylurea with a strong base such as sodium hydroxide in an aqueous medium.

The 4-amino-1,3-dialkyl uracil is then converted into 4-amino-5-nitroso-1,3-dialkyluracil by treating with sodium nitrite in glacial acetic acid at room temperature, according to the following reaction:

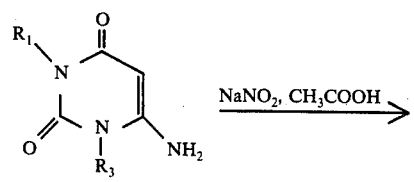

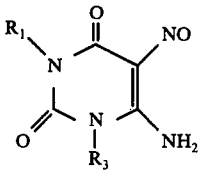

The 4-amino-5-nitroso-1,3-dialkyl-uracil is then reduced to a 4,5-diamino=1,3-dialkyluracil by reaction with sodium dithionite in ammonium hydroxide solution according to the following reaction:

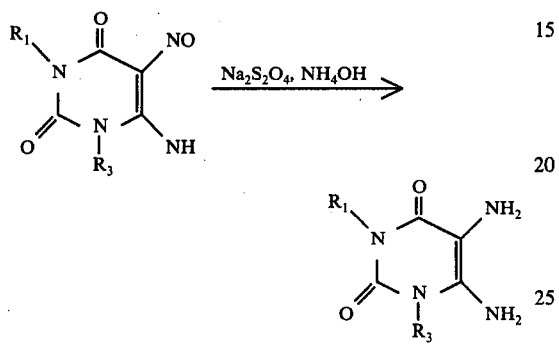

The 4,5-diamino-1,3-dialkyluracil is next converted to a 4-amino-5-alkylamino-1,3-dialkyluracil by reacting with a lower aliphatic acid according to the following equation:

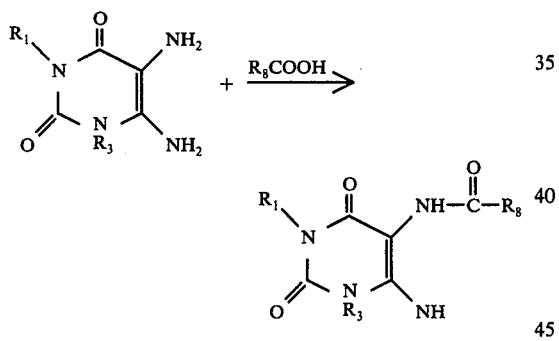

wherein $R_8$ is a lower group.

The 4-amino-5-alkanoylamino-1,3-dialkyluracil is then cyclized to form the 1,3,8-trialkylxanthine by heating in 10% aqueous sodium hydroxide solution to reflux temperature according to the following equation:

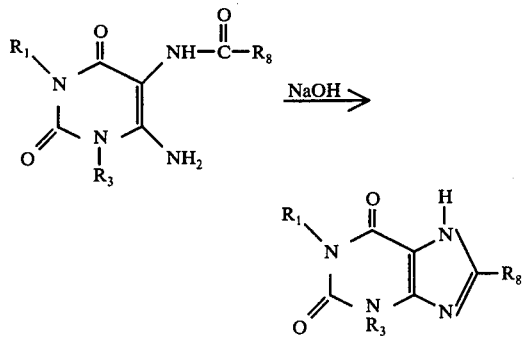

The compounds of this invention wherein $R_3$ contains an asymmetric carbon atom can exist in optically active enantiomeric forms. These forms may exist separately or mixed in any proportions. The racemic, or equimolar mixture of enantiomeric forms is obtained in the synthesis using reagents devoid of optical activity. The optically active forms of the substituted xanthines can be prepared by using the corresponding optically active amines $R_3NH_2$ in the synthesis. For example, the optically active dextro- or levo- form of the substituted xanthines having $R_3 = CH_2CH(CH_3)CH_2CH_3$ can be obtained by starting with the corresponding optically active form of 2-methylbutylamine. Dextro- and levo-2-methylbutylamines can be prepared by from the corresponding commercially available dextro- and levo-2-methylbutanols by the procedure described by Vasi, I. G., and Desai, R. K., *J. Inst. Chemists Calcutta*, 45, 66 (1973).

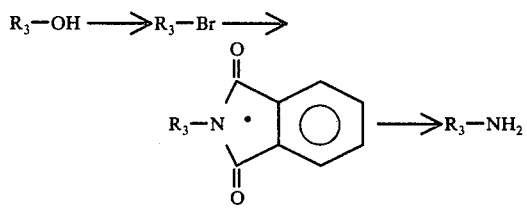

The compounds of this invention may be administered in the customary ways such as orally, sublingually, inhalation, rectally, and parenterally. Tablets, capsules, solutions, suspensions and aerosol mist may be used as forms for administration.

The compounds of this invention can be formulated into compressed tablets incorporating the customary inert excipients including diluents, binders, lubricants, disintegrants, colors, flavors, and sweetening agents. Commonly used pharmaceutical diluents such as calcium sulfate, lactose, kaolin, mannitol, sodium chloride, dry starch, and powdered sugar may be used.

Suitable binders for tablets include starch, gelatin, sugars, such as sucrose, glucose, lactose, molasses, natural and synthetic gums such as acacia, sodium alginate, extract of Irish moss, panwar gum, ghatti gum, carboxymethyl cellulose, polyvinylpyrrolidone and the like.

Commonly used lubricants which are suitable for tablets include talc, hydrogenated vegatable oils, and the like.

A suitable disintegrant may be incorporated into the tablets. Suitable disintegrants such as starches, clays, cellulose, algins, and gums may be used as is well known to those skilled in the art.

Conventional coloring agents such as pharmaceutically acceptable dyes and lakes and flavoring agents such as mannitol, lactose, or artificial sweetners may also be added to the tablet composition.

The compounds of this invention may also be administered orally contained in hard or soft capsules of gelatin or other suitable material. The compound of this invention may be present in the capsule alone or mixed with a suitable diluent such as lactose or starch.

The compounds of this invention may also be administered sublingually as rapidly disintegrating tablets or as troches or sublingual lozenges or pastilles. These dosage forms are prepared by mixing the active ingredient with flavored, rapidly dissolving or rapidly disintegrating excipients. For example a suitable base would comprise starch, lactose, sodium saccharin and talc.

Parenteral means can also be used for administering the compounds of this invention. They may be incorporated into implantable, slow-dissolving pellets or into aqueous injectable suspensions or solutions, or oily injectable media such as fixed oils. In general, the parenteral forms should be prepared just prior to use.

The compounds of this invention may also be administered by inhalation of a mist. The active compound may be dissolved or suspended in an aerosol propellant or suitable carrier liquid and loaded into a standard aerosol container with sufficient propellant to provide the proper pressure for dispensing the compound. These propellants are usually fluorinated or fluorochlorinated lower saturated alphatic hydrocarbons. The active ingredient is then dispensed through a special valve in the form of a fine mist which is inhaled.

The great potency of 1,8-dimethyl-3-(2-methyl-1-butyl)-7-carbomethoxyxanthine makes it a preferred compound for aerosol administration, like epinephrine and isoproterenol, to abort acute attacks. Aerosols of theophylline and its salts have been tried in the art, but the high doses required for these drugs to be efficacious and the resulting toxic reactions make this mode of administration impractical.

As is well-known in the pharmaceutical art, it is necessary in compounding dosage forms to avoid incompatibilities between ingredients. In formulating dosage forms containing the compounds of this invention, it is necessary to avoid combinations of ingredients which will result in the instablity of the active compound if the dosage forms are to be stored for long periods of time. The particular incompatibilities to be avoided to attain this goal will be evident to one skilled in the art for each particular dosage form. Thus, for example, aqueous dosage forms of these compounds cannot be stored for long periods of time; however, they are perfectly satisfactory dosage forms if prepared immediately before administration.

It is preferred to administer the bronchodilator and antiallergy compounds of this invention orally in the form of tablets or capsules. Preferred dosage ranges in humans are from 2 to 50 mg.

The following examples illustrate the practice of this invention but are not intended to limit its scope.

EXAMPLE 1

Synthesis of 1,8-dimethyl-3-(2-methyl-1-butyl) xanthine

Step 1

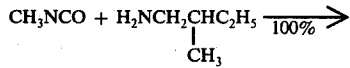

$$CH_3NCO + H_2NCH_2\underset{\underset{CH_3}{|}}{C}HC_2H_5 \xrightarrow{100\%}$$

$$CH_3NHCONHCH_2\underset{\underset{CH_3}{|}}{C}HC_2H_5$$

(1)

1.03 kg (11.8 mole) of 2-methyl-1-butylamine was added to 4.5 L of chloroform and the solution cooled to 0°–5° C.

Then 647.0 g (11.8 mole) of methyl isocyanate was added slowly while maintaining the temperature at 0.5° C.

After the addition was complete the reaction was allowed to reach room temperature. Stirring was continued for 18 hrs.

The chloroform was removed under vacuum to yield ~ 1.7 kg of 1-methyl-3-(2-methyl-1-butyl)urea (1) - an oil. Yield 100%.

Step 2

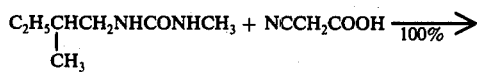

$$C_2H_5CHCH_2NHCONHCH_3 + NCCH_2COOH \xrightarrow{100\%}$$
$$\underset{CH_3}{|}$$

(1)

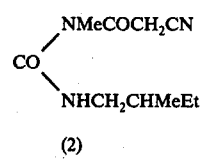

(2)

To ~ 1.7 kg (11.8 mole) of 1-methyl-3-(2-methyl-1-butyl)-urea (1) were added 4.3 L of acetic anhydride and 1.18 kg (13.9 mole) of cyanoacetic acid. This was heated for 2 hr. σ 60°–70° C.

The acetic anhydride was removed under vacuum to yield ~ 2.9 kg of an oil. This material is a mixture of cyano acetic acid and 1-methyl-1-cyanoacetyl-3-(2-methyl-1-butyl)urea (2) No attempt was made at purification; (2) was used immediately in the next step.

Step 3

4-amino-1-methyl-3-(2-methyl-1-butyl) uracil (3)

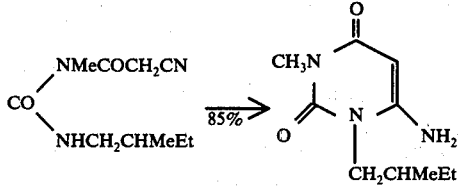

(2)          (3)

10.3 L of 10% NaOH solution was slowly added to 2.9 kg (11.8 mole) of crude 1-methyl-1-cyanoacetyl-3-(2-methyl-1-butyl) urea (2) with stirring.

The oil dissolved and shortly another oil precipitated. The temperature rose to ~ 60° C. and then dropped.

After stirring for awhile at room temperature the oil crystallized.

After cooling the product was filtered. The crude product was slurried in water and dried at 50° C. in vacuo to yield ~ 2.1 kg of 4-amino-1-methyl-3-(2-methyl-1-butyl) uracil (3) (m.p. 121°–124° C.). Yield 85% from (1).

Step 4

4-amino-5-nitroso-1-methyl-3-(2-methyl-1-butyl) uracil (4)

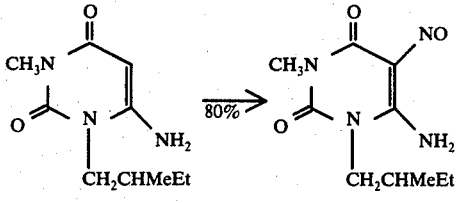

(3)          (4)

21. kg (9.9 mole) of 4-amino-1-methyl-3 (2-methyl-1-butyl)-uracil (3) was suspended in 22.0 L of water. A solution of 745.5 g (10.8 mole) of sodium nitrite in 5.7 L of water was added to the suspension. Then 1.2 L of glacial acetic acid was added dropwise and the suspension was stirred for 18 hr. at room temperature.

After cooling the precipitate was filtered. The crude product was slurried in water and dried at 80° C. in vacuo to yield ~ 1.9 kg of 4-amino-5-nitroso-1-methyl-3-(2-methyl-1-butyl)-uracil (4) (m.p. 202°–204° C.). Yield 80%.

Step 5

4,5-diamino-1-methyl-3-(2-methyl-1-butyl) uracil (5)

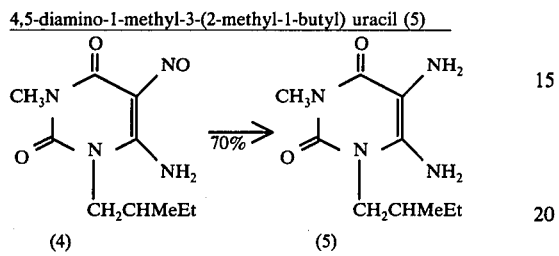

8.65 L of conc. ammonium hydroxide (58%) was added to 1.9 kg (7.9 mole) of 4-amino-5-nitroso-1-methyl-3-(2-methyl-1-butyl)uracil (4). An orange salt formed.

The suspension was placed in an oil bath at 80°–90° C. and a solution resulted.

5.6 kg (32.3 mole) of sodium dithionite was added in portions over about 30 min. When the addition was complete stirring was continued for 30 min.

The reaction was allowed to cool to room temperature and stirred overnight.

After cooling the precipitate was filtered, slurried with water and dried at 80° C. in vacuo to yield ~ 1.25 kg of 4,5-diamino-1-methyl-3-(2-methyl-1-butyl)uracil (5) (m.p. 161°–163° C.). Yield 70%.

Step 6

4-amino-5-acetylamino-1-methyl-3-(2-metyl-1-butyl) uracil (6)

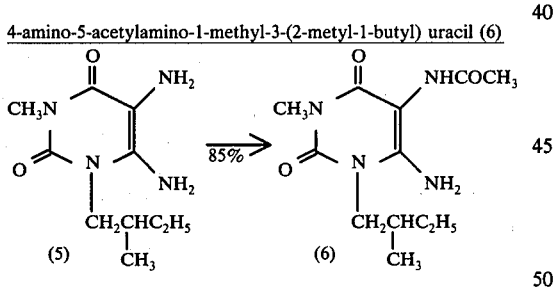

1.25 kg (5.5 mole) of 4,5-diamino-1-methyl-3-(2-methyl-1-butyl) uracil (5) was added to 4.5 L of glacial acetic acid and heated to reflux for 2 hrs.

The acetic acid was evaporated and the residue triturated with ether. The solid was filtered and dried at 60° C. in vacuo to yield ~ 1.26 kg of 4-amino-5-acetylamino-1-methyl-3-(2-methyl-1-butyl)uracil (6) (m.p. 178°–182° C.). Yield 85%.

Step 7

1,8-dimethyl-3-(2-methyl-1-butyl) xanthine (7)

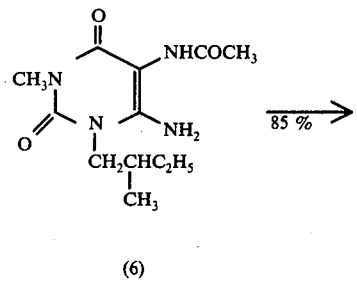

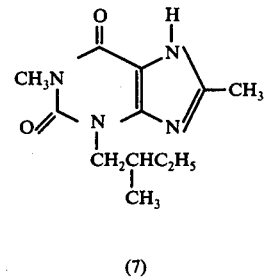

1.26 kg (4.7 mole) of 4-amino-5-acetylamino-1-methyl-3-(2-methyl-1-butyl)uracil (6) was added to 3.9 L of 10% sodium hydroxide solution and heated at reflux for 30 min.

The solution was filtered and the filtrate cooled to room temperature.

The pH of the filtrate was adjusted to 5.0 with glacial acetic acid.

After cooling the precipitate was filtered. The crude product was slurried twice with water and dried at 80° C. in vacuo to yield about 1.0 kg of 1,8-dimethyl-3-(2-methyl-1-butyl)xanthine (7) (m.p. 189°–191° C.). Yield 85%.

EXAMPLE 2

1,3-dialkylxanthines and 1,3,8-trialkylxanthines. By the procedure of Example 1 a number of 1,3-dialkylxanthines and 1,3,8-trialkylxanthines are synthesized. By proper choice of the reagents containing the precursors of the $R_1$, $R_3$ and $R_8$ groups the particular compounds are synthesized. $R_1$ and $R_3$ are determined by the reagents reacted in Step 1, $R_8$ is determined by the carboxylic acid reagent used in Step 5. Table 1 shows the reagents used in Steps 1 and 5 to introduce $R_1$, $R_3$, and $R_8$, and produce the listed compound.

TABLE 1

| No. | Compound | STEP 1 isocyanate | amine | STEP 5 acid |
|---|---|---|---|---|
| 6825 | 1-methyl-3-ethyl-xanthine | methyl isocyanate | methylamine | formic acid |
| 6826 | 1-methyl-3-n-propyl-xanthine | methyl isocyanate | n-propylamine | formic acid |
| 6762 | 1-methyl-3-isopropyl-xanthine | methyl isocyanate | isopropylamine | formic acid |
| 4315 | 1-methyl-3-(n-butyl)-xanthine | methyl isocyanate | n-butylamine | formic acid |
| 4258 | 1-methyl-3-(isobutyl)xanthine | methyl isocyanate | isobutylamine | formic acid |
| 6806 | 1-methyl-3-(n-pentyl)xanthine | methyl isocyanate | pentylamine | formic acid |
| 4280 | DL-1-methyl-3-(2- | methyl isocyanate | 2-methylbutylamine | formic acid |

TABLE 1-continued

| No. | Compound | isocyanate | amine | acid |
|---|---|---|---|---|
| | methyl-1-butyl)-xanthine | | | |
| 4340 | 1-methyl-3-(2,2-dimethyl-1-propyl)xanthine | methyl isocyanate | 2,2-dimethylpropylamine | formic acid |
| 4372 | DL-1-methyl-3-(2-methyl-1-pentyl)xanthine | methyl isocyanate | 2-methylpentylamine | formic acid |
| 4276 | DL-1-methyl-3-(2-ethyl-1-hexyl)xanthine | methyl isocyanate | 2-ethylhexylamine | formic acid |
| 4306 | 1-methyl-3-methallyl-xanthine | methyl isocyanate | methallylamine | formic acid |
| 6788 | 1-methyl-3-cyclohexyl-xanthine | methyl isocyanate | cyclohexylamine | formic acid |
| 4362 | 1-methyl-3-cyclohexyl-methylxanthine | methyl isocyanate | cyclohexanemethylamine | formic acid |
| 4296 | 1,3,8-trimethyl-xanthine | methyl isocyanate | methylamine | acetic acid |
| 6832 | 1,8-dimethyl-3-ethyl-xanthine | methyl isocyanate | ethylamine | acetic acid |
| 6834 | 1,8-dimethyl-3-n-propylxanthine | methyl isocyanate | n-propylamine | acetic acid |
| 6818 | 1,8-dimethyl-3-isopropylxanthine | methyl isocyanate | isopropylamine | acetic acid |
| 6840 | 1,8-dimethyl-3-(n-butyl)-xanthine | methyl isocyanate | n-butylamine | acetic acid |
| 6831 | 1,8-dimethyl-3-isobutylxanthine | methyl isocyanate | isobutylamine | acetic acid |
| 4506 | 1,8-dimethyl-3-n-pentylxanthine | methyl isocyanate | pentylamine | acetic acid |
| 4500 | 1,8-dimethyl-3-isopentylxanthine | methyl isocyanate | isopentylamine | acetic acid |
| 6738 | 1,8-dimethyl-3-(2,2-dimethylpropyl)-xanthine | methyl isocyanate | neopentylamine | acetic acid |
| 6842 | 1,8-dimethyl-3-n-hexyl)xanthine | methyl isocyanate | n-hexylamine | acetic acid |
| 4373 | 1,8-dimethyl-3-(2-methyl-1-pentyl)-xanthine | methyl isocyanate | 2-methyl-1-pentyl-amine | acetic acid |
| 6786 | 1,8-dimethyl-3-(2-methyl-1-hexyl)-xanthine | methyl isocyanate | 2-methyl-1-hexyl- | acetic acid |
| 6794 | 1,8-dimethyl-3-methylallyl-1-xanthine | methyl isocyanate | methallylamine | acetic acid |
| 6787 | 1,8-dimethyl-3-cyclohexylxanthine | methyl isocyanate | cyclohexylamine | acetic acid |
| 6778 | 1,8-dimethyl-3-cyclohexylmethylxanthine | methyl isocyanate | cyclohexanemethylamine | acetic acid |
| 6822 | 1,8-dimethyl-3-cyclopropylethylxanthine | methyl isocyanate | 2-cyclopropylethylamine | acetic acid |

| | | STEP 1 | | STEP 1 |
|---|---|---|---|---|
| No. | Compound | isocyanate | amine | acid |
| 4325 | 1,3-dimethyl-8-ethyl-xanthine | methyl isocyanate | methylamine | propionic acid |
| 4328 | 1,3-dimethyl-8-(n-propyl)xanthine | methyl isocyanate | methylamine | butyric acid |
| 4331 | 1,3-dimethyl-8-(isopropyl)xanthine | methyl isocyanate | methylamine | isobutyric acid |
| 4355 | 1,3-dimethyl-8-(cyclopropyl)xanthine | methyl isocyanate | methylamine | cyclopropane carboxylic acid |
| 4339 | 1,3-dimethyl-8-(n-butyl)xanthine | methyl isocyanate | methylamine | valeric acid |
| 4344 | 1,3-dimethyl-8-(isobutyl)xanthine | methyl isocyanate | methylamine | 3-methyl-butyric acid |
| 4345 | 1,3-dimethyl-8-(t-butyl)xanthine | methyl isocyanate | methylamine | 2,2-dimethyl-propionic acid |
| 4355 | 1,3-dimethyl-8-(cyclobutyl)xanthine | methyl isocyanate | methylamine | cyclobutyl-carboxylic acid |
| 6828 | DL-1-methyl-3-(2-methyl-1-butyl)-8-allylxanthine | methyl isocyanate | 2-methyl-1-butyl-amine | 3-butenoic acid |
| 6783 | DL-1-methyl-3-(2-methyl-1-butyl)-8-propargylxanthine | methyl isocyanate | 2-methyl-1-butyl amine | 3-butynoic acid |
| 6796 | D-1,8-dimethyl-3-(2-methyl-1-butyl)xanthine | methyl isocyanate | D-2-methyl-1-butyl amine | acetic acid |
| 6807 | L-1,8-dimethyl-3-(2-methyl-1-butyl)xanthine | methyl isocyanate | L-2-methyl-1-butyl amine | acetic acid |
| 4490 | DL-1-methyl-3-(2-methyl-1-butyl)-8-ethylxanthine | methyl isocyanate | 2-methyl-1-butyl-amine | propionic acid |
| 4489 | DL-1-ethyl-3-(2-methylbutyl-8-methylxanthine | ethyl isocyanate | 2-methyl-1-butyl-amine | acetic acid |
| 4495 | DL-1,8-diethyl-3-(2-methyl-1-butyl)xanthine | ethyl isocyanate | 2-methyl-1-butyl-amine | propionic acid |
| 4388 | 1,8-dimethyl-3- | methyl isocyanate | isobutylamine | acetic acid |

TABLE 1-continued isobutylxanthine

EXAMPLE 3

1,8-dimethyl-3-(2-methyl-1-butyl) xanthine-7-carboxylic acid, methyl ester

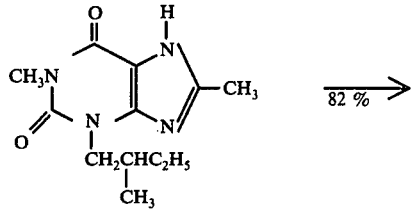

82% →

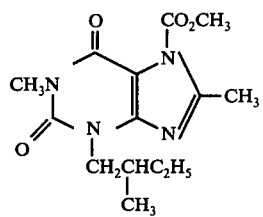

1.0 kg (4.0 mole) of 1,8-dimethyl-3-(2-methyl-1-butyl)-xanthine was suspended in 19.0 L of dry tetrahydrofuran.

288.0 g of sodium hydride (50% in oil) (6.0 mole) was washed with anhydrous ether and was then carefully added to the suspension.

The suspension was stirred for 1 hr (a solution resulted).

567.0 g (4.0 mole) of methyl chloroformate was slowly added.

After addition was complete the reaction was heated to reflux for 18 hrs.

Then the reaction was filtered hot. The filtrate was evaporated and the residue triturated with hexane. The resultant solid was washed with a little ether, filtered and dried at 40° C. in vacuo to yield ~ 1.0 kg of 1,8-dimethyl-3-(2-methyl-1-butyl)xanthine-7-carboxylic acid, methyl ester (m.p. 110°–112° C.). Yield 82%.

EXAMPLE 4

1,3,8-trialkylxanthine-7-carboxylic acid esters. By the procedure of Example 3 using the corresponding 1,3,8-trialkylxanthine and ester of chloroformic acid listed in Table 2, the 1,3,8-trialkylxanthine-7-carboxylic acid esters listed in Table 2 are prepared.

TABLE 2

| No. | PRODUCT | REAGENTS XANTHINE | CHLOROFORMIC ESTER |
|---|---|---|---|
| 4260 | 1,3-dimethylxanthine-7-carboxylic ester, methyl ester | 1,3-dimethylxanthine (theophylline) | methylchloroformate |
| 6862 | 1-methyl-3-ethylxanthine-7-carboxylic acid, methyl ester | 1-methyl-3-ethylxanthine | methylchloroformate |
| 6853 | 1-methyl-3-n-propylxanthine-7-carboxylic acid, methyl ester | 1-methyl-3-n-propyl-xanthine | methylchloroformate |
| 6884 | 1-methyl-3-isopropyl-xanthine-7-carboxylic acid, methyl ester | 1-methyl-3-isopropyl-xanthine | methylchloroformate |
| 6896 | 1-methyl-3-(n-butyl)-xanthine-7-carboxylic acid, methyl ester | 1-methyl-3-(n-butyl)-xanthine | methylchloroformate |
| 4274 | 1-methyl-3-(isobutyl) xanthine-7-carboxylic acid, methyl ester | 1-methyl-3-(isobutyl)-xanthine | methylchloroformate |
| 6865 | 1-methyl-3-(n-pentyl) xanthine-7-carboxylic acid, methyl ester | 1-methyl-3-(n-pentyl)-xanthine | methylchloroformate |
| 4380 | 1-methyl-3-(2-methyl-1-butyl)xanthine-7-carboxylic acid, methyl ester | 1-methyl-3-(2-methyl-1-butyl)xanthine | methylchloroformate |
| 6854 | 1-methyl-3-(2,2-dimethyl-1-propyl)xanthine-7-carboxylic acid, methyl ester | 1-methyl-3-(2,2-dimethyl-1-propyl)xanthine | methylchloroformate |
| 6857 | DL-1-methyl-3-(2-methyl-1-pentyl)xanthine-7-carboxylic acid, methyl ester | DL-1-methyl-3-(2-methyl-1-pentyl)xanthine | methylchloroformate |
| 6861 | DL-1-methyl-3-(2-methyl-1-hexyl)xanthine-7-carboxylic acid, methyl ester | DL-1-methyl-3-(2-methyl-1-hexyl)xanthine | methylchloroformate |
| 6882 | 1-methyl-3-methallylxanthine-7-carboxylic acid, methyl ester | 1-methyl-3-methallyl-xanthine | methylchloroformate |
| 6871 | 1-methyl-3-cyclohexyl-xanthine-7-carboxylic acid, methyl ester | 1-methyl-3-cyclohexyl-xanthine | methylchloroformate |
| 6877 | 1-methyl-3-cyclohexyl-methylxanthine-7-carboxylic acid, methyl ester | 1-methyl-3-cyclohexyl-methylxanthine | methylchloroformate |
| 4378 | 1,3,8-trimethylxanthine-7-carboxylic acid, methyl ester | 1,3,8-trimethylxanthine | methylchloroformate |
| 6866 | 1,8-dimethyl-3-ethylxanthine-7-carboxylic acid, methyl ester | 1,8-dimethyl-3-ethyl-xanthine | methylchloroformate |
| 6869 | 1,8-dimethyl-3-n-propyl-xanthine-7-carboxylic acid, | 1,8-dimethyl-3-n-propyl-xanthine | methylchloroformate |

TABLE 2-continued

| No. | PRODUCT | REAGENTS XANTHINE | CHLOROFORMIC ESTER |
|---|---|---|---|
| 6880 | 1,8-dimethyl-3-isopropyl-xanthine-7-carboxylic acid, methyl ester | 1,8-dimethyl-3-isopropyl-xanthine | methylchloroformate |
| 6892 | 1,8-dimethyl-3-(n-butyl)-xanthine-7-carboxylic acid, methyl ester | 1,8-dimethyl-3-(n-butyl)-xanthine | methylchloroformate |
| 4507 | 1,8-dimethyl-3-n-pentyl-xanthine-7-carboxylic acid, methyl ester | 1,8-dimethyl-3-n-pentyl-xanthine | methylchloroformate |
| 4505 | 1,8-dimethyl-3-isopentyl-xanthine-7-carboxylic acid, methyl ester | 1,8-dimethyl-3-isopentyl-xanthine | methylchloroformate |
| 6897 | 1,8-dimethyl-3-(2,2-dimethylpropyl)xanthine-7-carboxylic acid, methyl ester | 1,8-dimethyl-3-(2,2-dimethylpropyl)xanthine | methylchloroformate |
| 6850 | 1,8-dimethyl-3-n-hexyl)-xanthine-7-carboxylic acid, methyl ester | 1,8-dimethyl-3-n-hexyl)-xanthine | methylchloroformate |
| 4515 | DL-1,8-dimethyl-3-(2-methyl-1-pentyl)xanthine-7-carboxylic acid, methyl ester | DL-1,8-dimethyl-3-(2-methyl-1-pentyl)xanthine | methylchloroformate |
| 4390 | 1,8-dimethyl-3-isobutyl-xanthine-7-carboxylic acid, methyl ester | 1,8-dimethyl-3-isobutyl-xanthine | methylchloroformate |
| 6888 | DL-1,8-dimethyl-3-(2-methyl-1-hexyl)xanthine-7-carboxylic acid, methyl ester | DL-1,8-dimethyl-3-(2-methyl-1-hexyl)xanthine | methylchloroformate |
| 6906 | 1,8-dimethyl-3-methally-xanthine-7-carboxylic acid, methyl ester | 1,8-dimethyl-3-methyallyl-xanthine | methylchloroformate |
| 6878 | 1,8-dimethyl-3-cyclohexyl-xanthine-7-carboxylic acid, methyl ester | 1,8-dimethyl-3-cyclohexyl-xanthine | methylchloroformate |
| 6898 | 1,8-dimethyl-3-cyclohexyl-methylxanthine-7-carboxylic acid, methyl ester | 1,8-dimethyl-3-cyclohexyl-methylxanthine | methylchloroformate |
| 6911 | 1,8-dimethyl-3-cyclopropyl-ethylxanthine-7-carboxylic acid, methyl ester | 1,8-dimethyl-3-cyclopropyl-ethylxanthine | methylchloroformate |
| 6940 | 1,3-dimethyl-8-ethyl-xanthine-7-carboxylic acid, methyl ester | 1,3-dimethyl-8-ethyl-xanthine | methylchloroformate |
| 6957 | 1,3-dimethyl-8-(n-propyl)-xanthine-7-carboxylic acid, methyl ester | 1,3-dimethyl-8-(n-propyl)-xanthine | methylchloroformate |
| 6932 | 1,3-dimethyl-8-(isopropyl)-xanthine-7-carboxylic acid, methyl ester | 1,3-dimethyl-8-(isopropyl)-xanthine | methylchloroformate |
| 6947 | 1,3-dimethyl-8-(cyclopropyl)-xanthine-7-carboxylic acid, methyl ester | 1,3-dimethyl-8-(cyclo-propyl)xanthine | methylchloroformate |
| 6922 | 1,3-dimethyl-8-(n-butyl)-xanthine-7-carboxylic acid, methyl ester | 1,3-dimethyl-8-(n-butyl)-xanthine | methylchloroformate |
| 6951 | 1,3-dimethyl-8-(isobutyl)-xanthine-7-carboxylic acid, methyl ester | 1,3-dimethyl-8-(isobutyl)-xanthine | methylchloroformate |
| 6917 | 1,3-dimethyl-8-(t-butyl)-xanthine-7-carboxylic acid, methyl ester | 1,3-dimethyl-8-(t-butyl)-xanthine | methylchloroformate |
| 6914 | 1,3-dimethyl-8-(cyclobutyl)-xanthine-7-carboxylic acid, methyl ester | 1,3-dimethyl-8-(cyclo-butyl)xanthine | methylchloroformate |
| 6928 | DL-1-methyl-3-(2-methyl-1-butyl)-8-allylxanthine-7-carboxylic acid, methyl ester | DL-1-methyl-3-(2-methyl-1-butyl)-8-allylxanthine | methylchloroformate |
| 6933 | DL-1-methyl-3-(2-methyl-1-butyl)-8-propargylxanthine-7-carboxylic acid, methyl ester | DL-1-methyl-3-(2-methyl-1-butyl-8-propargyl-xanthine | methylchloroformate |
| 6919 | D-1,8-dimethyl-3-(2-methyl-1-butyl)xanthine-7-carboxylic acid, methyl ester | D-1,8-dimethyl-3-(2-methyl-1-butyl)xanthine | methylchloroformate |
| 6938 | L-1,8-dimethyl-3-(2-methyl-1-butyl(xanthine-7-carboxylic acid, methyl ester | L-1,8-dimethyl-3-(2-methyl-1-butyl)xanthine | methylchloroformate |
| 4491 | DL-1-methyl-3-(2-methyl-1-butyl)-8-ethyl-xanthine-7-carboxylic acid, methyl ester | DL-1-methyl-3-(2-methyl-1-butyl)-8-ethylxanthine | methylchloroformate |
| 4494 | DL-1-ethyl-3-(2-methyl-1-butyl)-8-methylxanthine-7-carboxylic acid, methyl ester | DL-1-ethyl-3-(2-methyl-1-butyl)-8-methylxanthine | methylchloroformate |
| 4498 | DL-1,8-diethyl-3-(2-methyl-1-butyl)xanthine-7-carboxylic acid, methyl ester | DL-1,8-diethyl-3-(2-methyl-1-butyl)xanthine | methylchloroformate |
| 4246 | 1,3-dimethylxanthine-7-carboxylic acid, ethyl ester | 1,3-dimethylxanthine | ethylchloroformate |
| 4356 | 1,3-dimethylxanthine-7-carboxylic acid, n-propyl | 1,3-dimethylxanthine (theophylline) | n-propyl chloroformate |

TABLE 2-continued

| No. | PRODUCT | REAGENTS | |
|---|---|---|---|
| | | XANTHINE | CHLOROFORMIC ESTER |
| | ester | | |
| 4361 | 1,3-dimethylxanthine-7-carboxylic acid, ispropyl ester | 1,3-dimethylxanthine (theophylline) | isopropyl chloroformate |
| 4275 | 1,3-dimethylxanthine-7-carboxylic acid, n-butyl ester | 1,3-dimethylxanthine (theophylline) | n-butyl chloroformate |
| 4273 | 1,3-dimethylxanthine-7-carboxylic acid, isobutyl ester | 1,3-dimethylxanthine (theophylline) | isobutyl chloroformate |
| 4477 | DL-1,8-dimethyl-3-(2-methyl-1-butyl)xanthine-7-carboxylic acid, ethyl ester | DL-1,8-dimethyl-3-(2-methyl-1-butyl) xanthine | ethyl chloroformate |
| 4488 | DL-1,8-dimethyl-3-(2-methyl-1-butyl)xanthine-7-carboxylic acid, n-propyl ester | DL-1,8-dimethyl-3-(2-methyl-1-butyl)xanthine | n-propyl chloroformate |
| 4278 | 1,3-dimethylxanthine-7-carboxylic acid, 2-chloroethyl ester | 1,3-dimethylxanthine | 2-chloroethylchloroformate |
| 4262 | 1,3-dimethylxanthine-7-carboxylic acid, phenyl ester | 1,3-dimethylxanthine | phenylchloroformate |
| 6852 | DL-1,8-dimethyl-3-(2-methyl-1-butyl)xanthine-7-carboxylic acid, 2-chloroethyl ester | DL-1,8-dimethyl-3-(2-methyl-1-butyl)xanthine | 2-chloroethyl-chloroformate |
| 6860 | DL-1,8-dimethyl-3-(2-methyl-1-butyl)xanthine-7-carboxylic acid, phenyl ester | DL-1,8-dimethyl-3-(2-methyl-1-butyl)xanthine | phenylchloroformate |

In the following comparative examples results of pharmacological tests with a number of the compounds of this invention and of the prior art are presented. The pharmacological properties were evaluated by standard tests which are defined, together with the symbols used as follows:

BD Bronchodilator activity evaluated against histamine-induced bronchoconstriction in the guinea pig, and expressed as % protection at the stated time interval (in minutes and hours) post-drug against histamine agonist. Doses are expressed in milligrams per kilogram of body weight (mpk) per os (po) or intraperitoneally (ip).

A modification of the method of Siegmund. O.H., et al., J. Pharmacol. and Exp. Therap. 90:254-9, 1947, is used. Healthy guinea pigs weighing from 250 to 300 grams are placed four at a time and separated by wiring screening in an 11 liter plastic chamber, at the time of peak activity following drug administration. The challenge consists of histamine diphosphate (1% solution) aerosolized in a de Vilbiss 40 nebulizer at 200 mm Hg. Times for prostration are recorded. All animals exposed to the aerosols for 10 minutes or longer without prostration, are arbitrarily considered fully protected.

Per cent protection is calculated as follows:

$$\% \text{ Protection} = \frac{100 \text{ (Test prostration time} - \text{control prostration time)}}{600 - \text{control prostration time}}$$

wherein the times are measured in seconds.

CP Cardiopulmonary activity evaluated against histamine-induced bronchoconstriction in the dog and expressed as % increase ( ↑ ) or decrease ( ↓ ) in the following parameters:
BP blood pressure
HR heart rate
PR pulmonary resistance
PC pulmonary compliance
RMV respiratory minute volume The method used is that of Giles, R. E., Finkel, N. P., and Mazurowski, J., Arch. Int. Pharmacodyn. Therap. 194, 213 (1971). A simulated asthmatic state is induced in anesthetized spontaneously breathing dogs by graded intravenous doses of histamine. The degree of induced bronchoconstriction is reflected by proportionate increases in pulmonary resistance. Pretreatment with bronchodilator drugs aims to block the bronchospastic response to histamine. Each dog serves as its own control. Mean values 2 hours post drug are given.

SP Spasmolytic activity evaluated in vitro using guinea pig tracheal chain preparation, and expressed as the molar (M) concentration required to produce maximum relaxation.

The method used in that of Castillo and de Beer, J. Pharmac. Expt. Therap. 90, 104, 1947.

AA Antiallergy (anti-anaphylactic) activity evaluated against antigen-induced bronchconstriction in rats sensitized with N. brasliensis, and expressed as % protection (R).

The method used in that of Church, N. K., Collier, H. O. J., and James, G. W. L., Brit. J. Pharmacol. 46, 56-65 (1972). Rats sensitized with antigen from Nippostrongylus brasiliensis exhibit anaphylactic shock when reexposed to this antigen 28 days later. The animals are subdivided into control and test groups. Test animals receive a drug either orally, intraperitoneally or intravenously and are challenged with intravenous antigen at fixed time intervals after dosing. Antigen-induced increases in tracheal pressure are monitored and reflect the extent of bronchoconstriction.

PCA Antianaphylactic activity against passive cutaneous anaphylaxis in the rat, expressed as % protection against antigen-induced wheal formation.

The method used is that of Ogilvie, B. M., Immunology 12, 113-131 (1967). Reaginic AgE antibodies develope in the rat following subcutaneous injection of Nippostrongylus brasiliensis larvae. Antisera, collected 28 days later are injected subcutaneously into new rats. These new rats when challenged with antigen 24 hours later exhibit an immediate type I reaction characterized by local swelling and edema (wheal) at the site of antisera injection.

$LD_{50}$ Dose required to cause death of 50% of test animals.

The LD$_{50}$ was determined in three species, the mouse (male, 18-25 g), the albino rat (female, 150-200 g) and the albino guinea pig (male 180-280 g) by oral administration and in the albino rat by intraperitoneal administration. The animals are fasted overnight prior to testing. Six groups of ten animals are used; five groups are dosed with the test substance, the sixth group serves as a control and receives the drug vehicle at the highest test concentration. The compounds were administered in a 0.5% gum tragacanth solution in distilled water using a constant logarithmic increment in dose. Dose volume ranged from 5 to 40 mg/kg.

corresponding compound devoid of the 7-carbomethoxy groups, 4296, gives only 53% protection at the larger dose of 100 mpK. Clearly, the 7-carbomethoxy derivative is superior. 4274 gives greater protection than 4258 at equal doses. In comparing 4387 and 4383 at equal doses (10 mpK) it can be seen that the 7-carbomethoxy compound 4387 shows greater activity. Although both of these compounds are already very potent, the benefit of the 7-carbomethoxy group is particularly evident in the dog at 1 mpK. Another comparison shows that 4260 is clearly superior to theophylline at the same dose (80 mpK).

TABLE 3

EFFECT OF 7-CARBOMETHOXY GROUP ON POTENCY

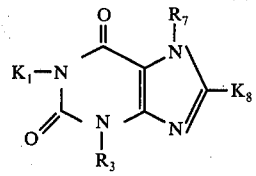

| CPD. | R$_1$ | R$_3$ | R$_8$ | R$_7$ | BD (guinea pig) mpK 30' 1h 2h 4h 6h 10h | AA (rat) mpK 1h | SP in vitro C | LD$_{50}$ mpK | spec |
|---|---|---|---|---|---|---|---|---|---|
| 4296 | CH$_3$ | CH$_3$ | CH$_3$ | H | 100po 53 45 43 23 150po 68 80 71 79 86 85 | 75ip 49 | M/14 | | |
| 4378 | CH$_3$ | CH$_3$ | CH$_3$ | COOCH$_3$ | 60po 96 95 89 | 75ip 54 | M/10 | | |
| 4258 | CH$_3$ | CH$_2$CHMe$_2$ | H | H | 15po 45 75 39 25po lethal 2/4 | 1.5ip 79 2.0ip tox | M/1000 | | |
| 4274 | CH$_3$ | CH$_2$CHMe$_2$ | H | COOCH$_3$ | 15po 92 87 64 18 40po lethal 1/6 | 5ip 74 | M/2000 | | |
| 4383 | CH$_3$ | CH$_2$CHMeEt | CH$_3$ | H | 10po 35 63 66 20po 92 100 97 | 2.5po 58 | M/1000 | 21.7po 24.6ip 88.7po 887.po 60.6po | g. pig rat rat rat mouse |
| 4387 | CH$_3$ | CH$_2$CHMeEt | CH$_3$ | COOCH$_3$ | 10po 44 87 59 37 20po 94 92 | 2.5po 72 5po 68 10po 57 5ip 55 75ip 70 | M/1000 | 27.4po 54.9po 18.3ip 60.0po | g. pig mouse rat rat |
| Theo-phylline | CH$_3$ | CH$_3$ | H | H | 80po 32 69 42 17 100po 45 58 36 25 14 | 25po 50 100po 73 | M/10 | 183po 225po 150ip | g. pig rat rat |
| 4260 | CH$_3$ | CH$_3$ | H | COOCH$_3$ | 80po 99 100 86 95 0 | 75ip 82 | M/20 | | |

The animals were housed five per cage (rat and guinea pig) or ten per cage (mouse) with free access to food and water. The number of dead animals was recorded daily for five consecutive days. The total mortality per group of ten for each dose level was recorded and and LD$_{50}$ with Confidence Limits calculated according to the method described by Weil, C. S., Biometrics 8(3): 249-263, 1952.

EXAMPLE 5

This example illustrates the superiority of 7-carboalkoxyxanthines over the corresponding 7-H xanthines. Several pairs of compounds were tested in a number of assays as described above.

The results may be seen in Table 4 wherein corresponding xanthines with and without the 7-carbomethoxy group are compared. The effect can be seen most clearly by comparing the potency of the compounds in the bronchodilation assay in the guinea pig (BD[guinea pig]).

In interpreting the BD data it should be noted that a dose giving less than 40-50% protection is not considered useful. Differences in percent protection of less than 10% are probably not significant. 4378 gives 96% protection at 1 hour at a dose of 60 mpK while the

EXAMPLE 6

This example illustrates the prolonged activity of the 8-alkylxanthines over that of the corresponding 8-H compounds. The increased & prolonged activity of the 1,3,8-trialkyl-7-carboalkoxyxanthines relative to that of the 1,3-dialkyl-7-carboalkoxyxanthines may be seen in Table 4 which compares the activity of corresponding pairs of substituted xanthines with and without 8-alkyl groups.

The data on bronchodilator activity in the guinea pig (BD[guinea pig]) show the prolonged activity of the compounds having an 8-alkyl group. In each pair the protection at 4 hours or 6 hours produced by the 8-methyl compound is greater than the protection by the corresponding compound devoid of the 8-methyl group. For pairs 4387 vs. 4380, 4390 vs. 4274, and 4378 vs. 4260, the 8-methyl derivatives are shown to be effective at lower doses and for longer duration that the 8-H compounds. This phenomenon is attributed to the 8-alkyl substitutent interfering with the normal bioinactivation of 1,3-dialkylxanthines by enzymatic oxidation at the 8-position, and was not anticipated by the teachings of the prior art on xanthine compounds.

TABLE 4
PROLONGED ACTIVITY OF 8-ALKYLXANTHINES

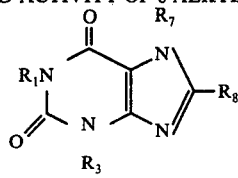

| CPD. | R₁ | R₃ | R₈ | R₇ | BD (guinea pig) mpK 30' 1h 2h 4h 6h 10h | AA (rat) mpK 1h | SP in vitro C | LD₅₀ mpK spec |
|---|---|---|---|---|---|---|---|---|
| 4274 | CH₃ | CH₂CHMe₂ | H | COOCH₃ | 15po 92 87 64 18<br>40po lethal 1/6 | 5ip 74 | M/2000 | |
| 4390 | CH₃ | CH₂CHMe₂ | CH₃ | COOCH₃ | 10po 49 86      79 48 | 2ip 60<br>4ip 52<br>2.5po 77 | M/1000 | 25.2po g. pig<br>27.6po mouse<br>9.1ip rat<br>33.5po rat |
| 4260 | CH₃ | CH₃ | H | COOCH₃ | 80po 99 100 86 95 0 | 75ip 82 | M/20 | |
| 4378 | CH₃ | CH₃ | CH₃ | COOCH₃ | 60po    96   95 89 | 75ip 54 | M/10 | |
| 4380 | CH₃ | CH₂CHMeEt | H | COOCH₃ | 40po 99   57 12<br>20po   64 | 5po 66 | M/700 | |
| 4387 | CH₃ | CH₂CHMeEt | CH₃ | COOCH₃ | 10po 44 87     59 37<br>20po    94    92 | 2.5po 72<br>5po 68<br>10po 57 | M/1000 | 27.4po g. pig<br>54.9po mouse<br>18.3ip rat<br>60.0po rat |

EXAMPLE 7

This example illustrates the decreased toxicity of substituted xanthines having R₃ = 2-methyl-1-butyl over those having R₃ = isobutyl while the potency of the compounds remains approximately equal.

The unexpected improvement in activity of 1-alkyl-3-(2-methyl-1-butyl)-7-carbomethoxy xanthines, without a corresponding increase in toxicity with reference to the corresponding 3-isobutyl homologs can be seen in Table 5 where the data for corresponding pairs of compounds is presented. This effect is seen most clearly in the pair 4387 vs. 4390. The effectiveness of the 7-carbomethoxy compounds can be compared in the bronchodilation assay in the guinea pig and in the antiallergy assay in the rat. The effectiveness data show that the 1-methyl-3-(2-methyl-1-butyl)-8-methyl-7-carbomethoxyxanthines (4387) is about as effective as the corresponding 3-isobutyl compound (4390) in the guinea pig, rat and dog assays. Yet 4387 is only about one-half as lethal as 4390 in the rat and mouse. Likewise, in the guinea pig toxic effects can be seen in the case of the xanthines having the 3-isobutyl group, while at the same dose the corresponding compound having the 3-(2-methyl-1-butyl) group is effective and non-toxic.

TABLE 5
EQUAL ACTIVITY WITHOUT INCREASED TOXICITY 3-(2-METHYLBUTYL) VS. 3-ISOBUTYL

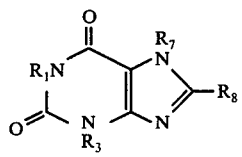

| Cpd. | R₁ | R₃ | R₈ | R₇ | BD (guinea pig) mpK 30' 1h 2h 4h 6h 10h | AA (rat) mpK 1h | SP in vitro C | LD₅₀ mpK spec. |
|---|---|---|---|---|---|---|---|---|
| 4390 | CH₃ | CH₂CHMe₂ | CH₃ | COOCH₃ | 10po   49 86     79 48<br>20po      lethal 1/2 | 2ip 60<br>4ip 52<br>2.5po 77 | M/1000 | 25.2po g. pig<br>27.6po mouse<br>9.1ip rat<br>33.5po rat |
| 4387 | CH₃ | CH₂CHMeEt | CH₃ | COOCH₃ | 10po   44 87     59 37<br>20po     94    92 | 2.5po 72<br>5po 68<br>10po 57<br>5ip 55 | M/1000 | 27.4po g. pig<br>54.9po mouse<br>18.3ip rat<br>60.0po rat |
| 4274 | CH₃ | CH₂CHMe₂ | H | COOCH₃ | 15po 92 87   64 18<br>40po     lethal 1/6 | 5ip 74 | M/2000 | |
| 4380 | CH₃ | CH₃CHMeEt | H | COOCH₃ | 40po     99   57 12<br>20po     64 | 5po 66 | M/700 | |

EXAMPLE 8

This example illustrates the activity of substituted xanthines according to this invention and the variation in pharmacological effects produced by introducing different R₃ substituents.

Table 6 shows the results of the bronchodilation assay described above in the guinea pig for a series of 1,3-dialkyl and 1,3,8-trialkylxanthine-7-carboxylates in which the R₃ group was varied. The most effective compounds are those in which the lowest dose produces an acceptable bronchodilation (~40%). Data is also included showing effectiveness in the antiallergy assay in the rat, and the in vitro bronchodilation activity.

The data for the effectiveness of the compounds shown in the Table 6 teaches that the activity of xanthine bronchodilators depends not only upon the total number of carbon atoms comprising $R_1$, $R_3$, $R_8$ and R, but also upon the distribution of these carbon atoms among $R_1$, $R_3$, $R_8$ and R, and especially upon the as in 2-methyl-1-butyl. Optimal activity, i.e., maximum activity with relatively lowest toxicity is obtained when $R_3$ is a 2-methyl-1-butyl group. Of all the possible $C_4$ and $C_5$ alkyl groups, only the 2-methyl-1-butyl group is both primary and asymmetric, i.e., capable of existing as dextro and levo forms.

TABLE 6
BRONCHODILATION ACTIVITY OF 1,3,8-TRIALKYL-7-CARBOMETHOXYXANTHINES

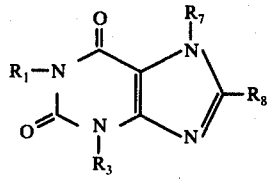

| CK | R | $R_3$ | $R_8$ | $R_7$ | mpK | 30' | 1h | 2h | 4h | 6h | 8h | 10h | AA (rat) mpK 1h | SP in vitro C |
|---|---|---|---|---|---|---|---|---|---|---|---|---|---|---|
| 4274 | $CH_3$ | $CH_2CHME_2$ | H | $COOCH_3$ | 15po | 92 | 87 | 64 | 18 | | | | 5ip 74 | M/2000 |
| | | | | | 40po | lethal 1/6 | | | | | | | | |
| 4380 | $CH_3$ | $CH_2CHMeEt$ | H | $COOCH_3$ | 40po | | 99 | | 57 | 12 | | | 5po 66 | M/700 |
| | | | | | | | 64 | | | | | | | |
| 4377 | $CH_3$ | $CH_2CHMePr$ | H | $COOCH_3$ | 80po | | 72 | 0 | | | | | | |
| | | | | | 20po | | 64 | | | | | | | |
| 4378 | $CH_3$ | $CH_3$ | $CH_3$ | $COOCH_3$ | 60po | | 96 | | 95 | 89 | | | 75ip 54 | M/10 |
| 4390 | $CH_3$ | $CH_2CHMe_2$ | $CH_3$ | $COOCH_3$ | | | | | | | | | 2ip 60 | M/1000 |
| | | | | | 10po | 49 | 86 | | 79 | | 48 | | 4ip 52 | |
| | | | | | | | | | | | | | 2.5po 77 | |
| 4387 | $CH_3$ | $CH_2CHMeEt$ | $CH_3$ | $COOCH_3$ | 10po | 44 | 87 | | 59 | | 37 | | | M/1000 |
| | | | | | 20po | | 94 | | 92 | | | | 2.5po 72 | |
| | | | | | | | | | | | | | 5po 68 | |
| | | | | | | | | | | | | | 10po 57 | |
| | | | | | | | | | | | | | 5ip 55 | |
| 4477 | $CH_3$ | $CH_2CHMeEt$ | $CH_3$ | $COOC_2H_5$ | 10po | 47 | 87 | | 50 | | | | | |
| 4488 | $CH_3$ | $CH_2CHMeEt$ | $CH_3$ | $COOC_3H_7$ (n) | 10po | | 24 | | 44 | | | | | |
| | | | | | 20po | | 78 | | 68 | | | | | |
| | | | | | 40po | | 100 | | 89 | | | | | |
| | | | | | 80po | lethal 1/4 | | | | | | | | |
| 4491 | $CH_3$ | $CH_2CHEt$ / Me | $C_2H_5$ | $COOCH_3$ | 10po | | 25 | | 21 | | | | | |
| | | | | | 40po | | 52 | | | | | | | |
| 4494 | $C_2H_5$ | $CH_2CHEt$ / Me | $CH_3$ | $COOCH_3$ | 10po | | 0 | | 49 | | | | | |
| | | | | | 40po | | 9 | | 80 | | | | | |
| | | | | | 80po | lethal 2/2 | | | | | | | | |
| 4498 | $C_2H_5$ | $CH_2CHEt$ / Me | $C_2H_5$ | $COOCH_3$ | 40po | | 15 | | 38 | | | | | |
| | | | | | 80po | | 63 | | 79 | | | | | |
| 4507 | $CH_3$ | $CH_2(CH_2)_3Me$ | $CH_3$ | $COOCH_3$ | 10po | | 26 | | — | | | | | |
| | | | | | 20po | | 52 | | — | | | | | |
| | | | | | 40po | | 100 | | 63 | | | | | |
| | | | | | 80po | lethal 2/2 | | | | | | | | |
| 4505 | $CH_3$ | $CH_2CH_2CHMe$ / Me | $CH_3$ | $COOCH_3$ | 10po | | — | | 15 | | | | | |
| | | | | | 40po | | — | | — | | | | | |
| | | | | | 80po | lethal 3/5 | | | | | | | | |
| 4515 | $CH_3$ | $CH_2CHCH_2Et$ / Me | $CH_3$ | $COOCH_3$ | 20po | | 7 | | — | | | | | |
| | | | | | 40po | | 100 | | — | | | | | | branching within the structure of the $R_3$ group.

Maximum activity is obtained when $R_1=R_8=R=$ methyl and $R_3$ is a $C_4$ or $C_5$ alkyl group. Peak activity is obtained when the alkyl group of $R_3$ is branched at the number 2 carbon

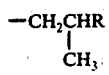

EXAMPLE 9

This example illustrates the antiallergy properties of the compounds of this invention.

1,8-Dimethyl-3-(2-methyl-1-butyl)-7-carbomethoxyxanthine and 1,8-dimethyl-3-isobutyl-7-carbomethoxyxanthine were tested in the rat passive cutaneous anaphylaxis screen described above. The data in Table 7 shows that these compounds are effective antiallergy agents.

TABLE 7
PERCENT PROTECTION IN THE RAT PASSIVE CUTANEOUS ANAPHYLAXIS SCREEN

| No. | Compound | Dose (mg/kg) & Route | Wheal Diameter (cm): Mean ± S.E.M. | | | Wheal Intensity: Mean ± S.E.M. | | |
|---|---|---|---|---|---|---|---|---|
| | | | Control | Response | % Δ | Control | Response | % Δ |
| 4387 | 1,8-dimethyl-3-(2-methyl-1-butyl)-7-carbomethoxyxanthine | 10po | 2.39 ± 0.10 | 1.41 ± 0.17 | 41 | 2.46 ± 0.13 | 1.65 ± 0.20 | 33 |
| | | 20po | 1.90 ± 0.15 | 0.81 ± 0.13 | 57 | 1.91 ± 0.21 | 1.18 ± 0.21 | 38 |
| 4380 | 1,8-dimethyl-3-isobutyl-7- | 20po | 1.86 ± 0.15 | 0.74 ± 0.21 | 60 | 2.35 ± 0.21 | 1.10 ± 0.23 | 53 |

TABLE 7-continued

| | | Dose (mg/kg) | Wheal Diameter (cm): Mean ± S.E.M. Wheal Intensity: Mean ± S.E.M. | | | | | |
|---|---|---|---|---|---|---|---|---|
| No. | Compound | & Route | Control | Response | % Δ | Control | Response | % Δ |
| | carbomethoxyxanthine | | | | | | | |

EXAMPLE 10

This example illustrates the effectiveness of the compounds of this invention in the dog.

The results of studies of cardiopulmonary activity in the dog by the above described procedures are shown in Table 8. The data show that compounds 4390 and 4387 significantly reduce the decrease in pulmonary compliance and increase in pulmonary resistance due to histamine administration. The corresponding values for theophylline, a clinically used xanthine bronchodilator, are shown for comparison. It can be seen that the compounds of this invention are more potent bronchodilators than theophylline in the dog.

TABLE 8

CARDIOPULMONARY ACTIVITY IN THE DOG

| | | CP (dog) (mean value at 2h) | | | | |
|---|---|---|---|---|---|---|
| | mpK | BP | HR | PC | PR | RMV |
| 4387 | 1po | ↓17 | ↑40 | ↑40 | ↓61 | ↑39 |
| | 2po | ↓03 | ↑16 | ↑60 | ↓85 | ↑10 |
| | 3po | ↓08 | ↑08 | ↑74 | ↓100 | ↑68 |
| | 4po | ↓25 | ↑17 | ↑42 | ↓77 | ↑76 |
| 4390 | 3po | ↓07 | ↑13 | ↑70 | ↓85 | ↑41 |
| Theophylline | 40po | ↓08 | ↑06 | ↑25 | ↓36 | ↑38 |

EXAMPLE 11

Tablets 19.5 grams of starch are dried to a moisture content of 10%. 0.5 grams of 1,8-dimethyl-3-(2-methyl-1-butyl)-7-carbomethoxyxanthine in finely powdered form are thoroughly mixed with the starch. The mixture is compressed into slugs. The slugs are reground into powder of 14–16 mesh size. This powder is recompressed into tablets weighing 200 mg. each. Each tablet thus has the composition:

1,8-dimethyl-3-(2-methyl-1-butyl)-7-carbomethoxyxanthine; 5 mg
Starch; 195 mg

EXAMPLE 12

Capsules

A dry mixuture os 19.5 grams of starch and 0.5 grams of 1,8-dimethyl-3-(2-methyl-1-butyl)-7-carbomethoxyxanthine is prepared as described in Example 10. The powder is loaded into hard gelatin capsules so that each capsule contains 200 mg of the powder.

EXAMPLE 13

Sublingual Tablets

Tablets for sublingual administration were prepared by standard procedure, each tablet containing 5 mg of 1,8-dimethyl-3-(2-methyl-1-butyl)-7-carbomethoxyxanthine in a rapidly disintegrating base comprising starch, lactose, sodium saccharin and talcum.

EXAMPLE 14

Aerosol

Five grams of 1,8-dimethyl-3-(2-methyl-1-butyl)-7-carbomethoxyxanthine were dissolved in 1000 grams of a mixture of 20 parts by weight of dichlorodifluoromethane and 80 parts by weight of 1,2-dichloro-1,1,2,2-tetrafluoroethane and loaded into a conventional aerosol medication dispenser to provide a means of administering the active ingredient by inhalation.

I claim:

1. A compound having the formula:

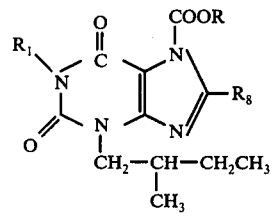

wherein
$R_1 = C_1-C_2$ alkyl
$R_8 = H$, $C_1-C_4$ alkyl
$R = C_1-C_4$ alkyl, 2-halo-($C_2-C_3$ alkyl), or phenyl 2. A compound according to claim 1 wherein $R_8$ is ethyl.

3. A compound according to claim 1 wherein $R_8$ is methyl.

4. A compound according to claim 1 wherein R is ethyl.

5. A compound according to claim 1 wherein R is methyl.

6. 1,8-dimethyl-3-(2-methyl-1-butyl)-7-carbomethoxyxanthine.

7. dextro-1,8-dimethyl-3-(2-methyl-1-butyl)-7-carbomethoxyxanthine.

8. levo-1,8-dimethyl-3-(2-methyl-1-butyl)-7-carbomethoxyxanthine.

9. 1,8-dimethyl-3-(2-methyl-1-butyl)-7-carboethoxyxanthine.

10. dextro-1,8-dimethyl-3-(2-methyl-1-butyl)-7-carboethoxyxanthine.

11. levo-1,8-dimethyl-3-(2-methyl-1-butyl)-7-carboethoxyxanthine.

12. 1,8-dimethyl-3-(2-methyl-1-butyl)-7-carbopropoxyxanthine.

13. 1-methyl-3-(2-methyl-1-butyl)-7-carbomethoxyxanthine.

14. dextro-1-methyl-3-(2-methyl-1-butyl)-7-carbomethoxyxanthine.

15. levo-1-methyl-3-(2-methyl-1-butyl)-7-carbomethoxyxanthine.

16. A pharmaceutical composition comprising an amount effective for bronchodilation of a compound of the formula:

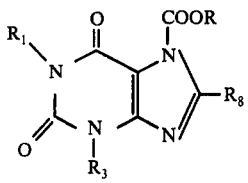

wherein
$R_1$ = $C_1$-$C_2$ alkyl
$R_3$ = $CH_2$—($C_3$-$C_4$ alkyl), $CH_2$—($C_3$-$C_4$ alkenyl), $CH_2$—($C_3$-$C_4$—cyclo—alkyl)
$R_8$ = H, $C_1$-$C_4$ alkyl
R = $C_1$-$C_4$ alkyl, 2-halo—($C_2$-$C_3$ alkyl), or phenyl
in combination with a non-toxic inert pharmaceutically acceptable diluent to give a dosage form selected from tablets, capsules, or aerosol mists.

17. A composition according to claim 16 in the form of a tablet.

18. A composition according to claim 16 in the form of a capsule.

19. A composition according to claim 16 in the form of a sublingual tablet.

20. A composition according to claim 16 wherein said diluent is an aerosol propellant.

21. A composition according to claim 16 comprising 1,8-dimethyl-3-(2-methyl-1-butyl)-7-carbomethoxyxanthine dissolved in a pharmaceutically acceptable aerosol propellant.

22. A pharmaceutical composition in the form of a tablet comprising between 2 mg and 50 mg of a compound according to claim 16 in combination with non-toxic pharmaceutically acceptable excipients.

23. The method of producing bronchodilation and suppressing the release of allergic mediators in mammals by administering to a mammal in need thereof an effective amount of a substituted xanthine having the formula:

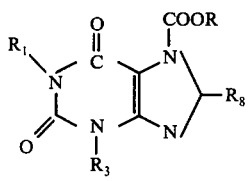

wherein
$R_1$ = $C_1$-$C_3$ alkyl,
$R_3$ = $C_1$-$C_7$ alkyl, $C_3$-$C_7$ alkenyl, $C_3$-$C_7$ alkynyl, $C_3$-$C_6$ cycloalkyl or $C_4$-$C_7$ cycloalkylalkyl,
$R_8$ = H, $C_1$-$C_4$ alkyl, $C_3$-$C_4$ alkenyl, $C_3$-$C_4$ alkynyl, or $C_3$-$C_4$ cycloalkylalkyl
R = $C_1$-$C_4$ alkyl, 2-halo $C_2$-$C_3$ alkyl, or phenyl 24. A method according to claim 23 wherein $R_1$ is methyl.

25. A method according to claim 23 wherein $R_3$ is —$CH_2$($C_1$-$C_6$ alkyl).

26. A method according to claim 23 wherein $R_3$ is —$CH_2$—($C_3$-$C_6$ cycloalkyl).

27. A method according to claim 23 wherein $R_3$ is selected from the group consisting of methyl, ethyl, n-propyl, methallyl, n-butyl, isobutyl, n-pentyl, 2-methyl-1-butyl, 3-methyl-1-butyl, 2,2-dimethylpropyl, 2-methyl-1-pentyl, cyclopropylmethyl, and cyclobutylmethyl.

28. A method according to claim 23 wherein $R_3$ is 2-methyl-1-butyl.

29. A method according to claim 23 wherein $R_3$ is isobutyl.

30. A method according to claim 23 wherein $R_8$ is $C_1$-$C_4$ alkyl.

31. A method according to claim 30 wherein $R_8$ is methyl.

32. A method according to claim 23 wherein R is $C_1$-$C_4$ alkyl.

33. A method according to claim 32 wherein R is methyl.

34. A method according to claim 32 wherein R is ethyl.

35. A method according to claim 23 wherein said substituted xanthine is dl-1,8-dimethyl-3-(2-methyl-1-butyl)-7-carbomethoxyxanthine.

36. A method according to claim 23 wherein said substituted xanthine is dextro-1,8-dimethyl-3-(2-methyl-1-butyl)-7-carbomethoxyxanthine.

37. A method according to claim 23 wherein said substituted xanthine is levo-1,8-dimethyl-3-(2-methyl-1-butyl)-7-carbomethoxyxanthine.

38. A method according to claim 23 wherein said substituted xanthine is 1,8-dimethyl-3-(2-methyl-1-butyl)-7-carboethoxyxanthine.

39. A method according to claim 23 wherein said substituted xanthine is 1,8-dimethyl-3-(2-methyl-1-butyl)-7-carbopropoxyxanthine.

40. A method according to claim 23 wherein said substituted xanthine is 1,8-dimethyl-3-isobutyl-7-carbomethoxyxanthine.

41. A method according to claim 23 wherein said substituted xanthine is 1,8-dimethyl-3-isobutyl-7-carboethoxyxanthine.

42. A method according to claim 23 wherein said substituted xanthine is administered to humans in a dose of between 0.2 and 200 mg.

43. A method according to claim 23 wherein said substituted xanthine is incorporated with inert excipients into a capsule and administered orally.

44. A method according to claim 23 wherein said substituted xanthine is incorporated with inert excipients into a tablet and administered orally.

45. A method according to claim 23 wherein said substituted xanthine is incorporated with inert excipients into a rapidly disintegrating tablet and administered sublingually.

46. A method according to claim 23 wherein said substituted xanthine is incorporated with propellant and solvent into an aerosol and administered by inhalation of the mist.

47. A method according to claim 23 wherein said substituted xanthine is incorporated with fatty vehicles into a suppository and administered rectally.

48. A method according to claim 23 wherein said substituted xanthine is incorporated with a sterilized vehicle prepared just prior to use and administered parenterally.

* * * * *

UNITED STATES PATENT AND TRADEMARK OFFICE
CERTIFICATE OF CORRECTION

PATENT NO. : 4,120,947  
DATED : October 17, 1978  
INVENTOR(S) : Julius Diamond Page 1 of 2

It is certified that error appears in the above-identified patent and that said Letters Patent are hereby corrected as shown below:

Column 1, line 28, "minmetic" should read --mimetic--. Column 1, line 33 and line 45, "Corticosteriod" should read --Corticosteroid--. Column 2, line 30, "hot" should read --not--. Column 2, line 57, "chospatic" should read --chospastic--. Column 7, line 11, "4,5-diamino=" should read -- 4,5-diamino- --. Column 7, lines 17 and 44 in the lower right hand portion of the structural formulas, "NH" should read --$NH_2$--. Column 7, line 29, "5-alkylamino" should read --5-alkanoylamino--. Column 8, line 11, delete "by". Column 8, line 53, "sweetners" should read --sweeteners--. Column 10, line 22, "σ" should read --at--. Column 11, line 41, "2-metyl" should read --2-methyl--. Column 13, Table 1, 4th column, compound 18, under "2-methyl-1-hexyl-" add --amine--. Columns 13-14, repeat of headings at middle of page, the last heading, "STEP 1" should read --STEP 5--. Column 17, line 30, columns of 2 and 3 of the table, "methally" and "methyallyl" should both read --methallyl--. Column 19, line 46, "40" should read --#40--. Column 21, line 49, delete second "and". Column 22, Table 3, in SP in vitro column, delete "88.7po"; in $LD_{50}$-mpk column, "887.po" should read --88.7po--. Column 23, Table 4, the portion of the table under "BD (guinea pig)" should read as follows:

| mpk | 30' | 1h | 2h | 4h | 6h | 10h |
|---|---|---|---|---|---|---|
| 15po | 92 | 87 | 64 | 18 | | |
| 40po | lethal 1/6 | | | | | |
| 10po | 49 | 86 | | | 79 | 48 |
| 80po | 99 | 100 | 86 | 95 | 0 | |
| 60po | | 96 | | 95 | 89 | |
| 40po | | 99 | | 57 | 12 | |
| 20po | | 64 | | | | |
| 10po | 44 | 87 | | | 59 | 37 |
| 20po | | 94 | | | 92 | |

UNITED STATES PATENT AND TRADEMARK OFFICE
CERTIFICATE OF CORRECTION

PATENT NO. : 4,120,947

DATED : October 17, 1978

INVENTOR(S) : Julius Diamond

It is certified that error appears in the above-identified patent and that said Letters Patent are hereby corrected as shown below:

Column 23, Table 5, in $R_3$ column, the last entry should read "$CH_2CHMeEt$." Column 25, Table 6, in $R_3$ Column, the first entry should read "$CH_2CHMe_2$"; in BD (guinea pig) - mpk column, after second "40po", insert --20po--. Column 26, Table 7, "Wheal Diameter" and "Wheal Intensity" headings should be in a line instead of a column. Column 27, line 50, "os" should read --of--. Column 27, line 52, "Example 10" should read --Example 11--. Column 29, Claim 23, in the formula, add a double bond to the right hand ring so that the formula reads as follows:

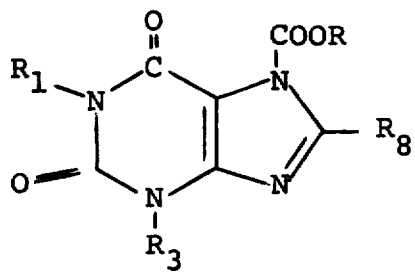

Signed and Sealed this

Fourth Day of March 1980

[SEAL]

Attest:

SIDNEY A. DIAMOND

Attesting Officer

Commissioner of Patents and Trademarks